United States Patent [19]

Cobb

[11] Patent Number: 4,599,472
[45] Date of Patent: Jul. 8, 1986

[54] PURIFICATION OF IODINE-CONTAINING MIXTURES AND COMPOSITIONS USEFUL THEREFOR

[75] Inventor: Raymond L. Cobb, Bartlesville, Okla.

[73] Assignee: Phillips Petroleum Company, Bartlesville, Okla.

[21] Appl. No.: 749,361

[22] Filed: Jun. 27, 1985

[51] Int. Cl.$^4$ ............................ C07C 2/64; C07C 2/68
[52] U.S. Cl. .................................. 585/459; 208/262; 208/295; 208/296; 585/462; 585/845; 585/848; 585/850; 585/855
[58] Field of Search ............... 585/459, 462, 845, 848, 585/850, 855, 833; 208/262, 295, 296

[56] References Cited

U.S. PATENT DOCUMENTS

| 2,535,735 | 12/1950 | Groebe et al. | 208/262 |
| 2,952,720 | 9/1960 | Peterson | 208/262 |
| 3,097,157 | 7/1963 | Accountius | 208/262 |
| 3,394,078 | 7/1968 | Peurifoy et al. | 585/850 |
| 3,488,923 | 1/1970 | Hutchinson | 55/71 |
| 3,772,156 | 11/1973 | Johnson et al. | 203/33 |
| 4,551,573 | 11/1985 | Cobb | 585/459 |

FOREIGN PATENT DOCUMENTS 2097421 11/1982 United Kingdom ............... 585/850

Primary Examiner—Andrew H. Metz
Assistant Examiner—A. Pal
Attorney, Agent, or Firm—Stephen E. Reiter

[57] ABSTRACT

Hydrocarbon solutions containing iodine or iodine-containing impurities are rendered essentially color-free by distillation in the presence of small amounts of a hydrocarbon soluble organometallic compound.

6 Claims, No Drawings

PURIFICATION OF IODINE-CONTAINING MIXTURES AND COMPOSITIONS USEFUL THEREFOR

This invention relates to alkylation processes. In another aspect, this invention relates to the purification of alkylated aromatic compounds. In yet another aspect, this invention relates to the purification of mixtures containing iodine or iodine forming impurities.

BACKGROUND

Aromatic compounds can be alkylated with olefinically unsaturated compounds employing a catalyst consisting essentially of aluminum halide and molecular iodine. Additionally, molecular iodine or iodine-containing compounds are useful in other catalytic conversions such as for example, Grignard reactions, carbonylation reactions, and the like. A problem encountered with such reactions is the removal of the iodine components from the reaction mixture so that color formation in the product is avoided. Methods disclosed in the prior art, such as for example, extraction with thiosulfate or bisulfite; treatment with other oxidants; distillation in the presence of acid or base, however, are not always successful in completely removing color forming impurities from the reaction mixture which contains the desired product.

OBJECT OF THE INVENTION

An object of the invention, therefore, is the preparation of alkyl aromatic hydrocarbon products free of color-forming impurities.

Another object of the invention is the removal of color-forming impurities from hydrocarbon solutions containing elemental iodine or precursors thereof.

These and other objects of my invention will become more apparent from the disclosure and claims herein provided.

STATEMENT OF THE INVENTION

In accordance with the present invention, I have discovered that the addition of small amounts of hydrocarbon soluble organometallic compounds to reaction mixtures comprising hydrocarbon product and at least one color-forming impurity containing iodine allows for the recovery by distillation of essentially colorless hydrocarbon product.

In accordance with another embodiment of the present invention, I have discovered that essentially color-free alkyl aromatic hydrocarbon product can be obtained by (1) contacting at least one olefinic compound with at least one aromatic compound in the presence of a catalyst consisting essentially of aluminum halide ($AlX_3$) and molecular iodine ($I_2$).

(2) washing the product mixture obtained from step (1) with aqueous caustic to remove the $AlX_3$, and separating a washed organic layer therefrom, (3) adding small amounts of a hydrocarbon soluble organometallic compound to the washed organic layer, and thereafter (4) subjecting the mixture produced in step (3) to distillation.

In accordance with yet another embodiment of my invention, I have discovered novel compositions of matter consisting essentially of (a) at least one alkyl aromatic hydrocarbon, (b) at least one iodine-containing compound, and (c) small amounts of a hydrocarbon soluble organometallic compound.

DETAILED DESCRIPTION OF THE INVENTION

In accordance with one embodiment of the present invention, a distillation process is provided for the purification of hydrocarbon-containing solutions which contain color-forming impurities by distilling the hydrocarbon from a mixture to which small amounts of a hydrocarbon soluble organometallic compound has been added. Since the presence of iodine or iodine-containing compounds is encountered in many reaction mixtures, it is contemplated that the present invention will find wide utility in the purification of organic compounds.

A preferred mixture for use in the practice of the present invention is a mixture comprising (i) a hydrocarbon product having about 8 up to 30 carbon atoms, and (ii) at least one color-forming impurity selected from the group consisting of:

$I_2$, and

R—I, wherein R is H or an organic radical having 1-30 carbon atoms, inclusive. Such compounds can be obtained from a variety of sources and by a variety of synthetic reactions. It is of course recognized by those of skill in the art that even if such color-forming impurities are present in very low concentrations, the practice of the present invention will be of value. Thus, even where the quantities of color-forming impurities in the mixture to be treated are so low as to be undetectable by conventional analytical techniques, such as for example, gas liquid chromatography, it will be desirable to employ the invention purification process to prevent later color formation upon storage of the purified product.

An especially preferred source of the mixture to be treated in accordance with the present invention is the alkylated aromatic products obtained by alkylation of aromatic compounds with olefins. The products obtained from such alkylation reactions have the following general formulas:

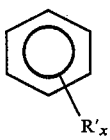

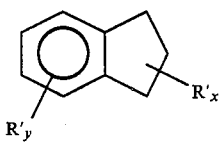

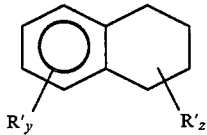

wherein each R' is independently a $C_1-C_{30}$ alkyl or cycloalkyl radical, x is an integer from at least 1 up to 6, y is an integer from 0 to 4, and z is an integer from at least 1 up to 8. Examples of alkyl aromatic products which can be purified in accordance with the present invention include hexamethyltetralin, n-propyltetramethylindane, pentamethylindane, tetramethylindane, heptamethylindane, neopentyltetramethylindane, hexamethylindane, ethyltetramethylindane, isopropyl tetramethylindane, ditertiarybutyltoluene, tertiarybutyl-m-xylene, and the like.

In accordance with the present invention, product free of color-forming impurities is obtained by distilling the mixture containing color-forming impurities in the presence of small amounts of a metal compound having the formula:

M—R″ wherein M is any metal such that the complex $MI_n$ formed in the process of the invention is non-volatile and essentially non-decomposable under the distillation conditions used for recovery of the desired product. Preferably, M is Cu, Fe, Co, or Zn; R″ is an anionic organic radical having 2–30 carbon atoms such that M—R″ forms a salt which is at least sparingly soluble in the hydrocarbon-containing reaction mixture which is to be distilled; and n represents the valence of the particular metal, e.g. if a Zn(II) compound is used, n=2; if a Cu(I) compound is used, n=1, and so forth. Those of skill in the art recognize that organometallic compounds which conform to the above formula can be generated in situ by providing a suitable metal in elemental (and preferably finely divided) form to the mixture which contains color-forming impurity.

Although suitable amounts of hydrocarbon soluble organometallic compound to be employed can be readily determined by those of skill in the art, generally at least about 0.01 to 1.0 weight percent of M—R″ will be employed with about 0.02 to 0.1 weight percent of hydrocarbon soluble organometallic compound based on total weight of mixture treated preferred.

While several different elements may be employed as component M, zinc is the presently preferred element to employ because of good distillation results obtained with zinc salts and the relative lack of corrosive effects on process equipment when zinc salts are employed.

R″ may be chosen from a wide variety of anionic radicals so long as the resulting compound M—R″ is at least sparingly soluble in the hydrocarbon-containing mixture to be treated in accordance with the present invention. Examples of suitable R″ radicals include $ACO_2$—, wherein A is a $C_1$–$C_{10}$ carbon radical; acetylacetonate; naphthenate; tallate; sulfonate; and the like.

In accordance with a specific embodiment of the invention, the alkyl aromatic product to be purified is prepared by the reaction of (a) at least one monocyclic, bicyclic or tricyclic aromatic compound having 6 up to 30 carbon atoms and (b) at least one olefinic compound; wherein said olefinic compound has 4 up to about 30 carbon atoms, and wherein said olefinic compound is capable of forming a tertiary carbocation under the process conditions in the presence of a catalyst consisting essentially of (i) $AlX_3$ and
(ii) $I_2$;

where each X is individually selected from the halogens.

Suitable aromatic compounds are broadly contemplated to include those compounds which are capable of undergoing Friedel-Crafts alkylation reaction. Thus, monocyclic as well as polycyclic aromatic compounds are suitable for the practice of the invention. Preferably, the aromatic compounds employed in the practice of the invention will be monocyclic, bicyclic or tricyclic aromatic compounds having 6 up to about 30 carbon atoms. Thus, benzene, naphthalene, anthracene, phenanthrene, and derivatives thereof are contemplated to be within the scope of the present invention.

An especially preferred group of aromatic compounds useful in the practice of my invention conform to the general formula

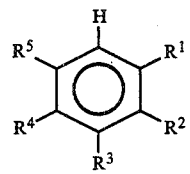

wherein each $R^1$, $R^2$, $R^3$, $R^4$, and $R^5$ is independently selected from hydrogen, and $C_1$ through $C_{10}$ alkyl or cycloalkyl radicals. When aromatic compounds which conform to the above formula are used for alkylation reactions, a variety of useful chemical intermediate and chemical products can be obtained.

Examples of aromatic compounds which satisfy the above formula include benzene, toluene, meta-xylene, tertiary-butylbenzene, and the like.

When it is desired that the aromatic compound yield a cyclialkylated aromatic product upon alkylation, then it is preferred that $R^1$ in the above formula be methyl, or ethyl and that $R^4$ be a secondary alkyl group having 3 to about 10 carbon atoms and only one alpha-hydrogen. Examples of aromatic compounds useful for the cyclialkylation reaction include para-cymene (para-isopropyltoluene), para-methylcyclohexylbenzene, para-methylcyclopentylbenzene, para-ethylcyclopentylbenzene, para-ethylcyclohexylbenzene and the like.

Suitable olefinic compounds are broadly contemplated to be organic compounds having at least one carbon-carbon double bond and any substituents which do not detrimentally interact with the catalyst employed for the alkylation reaction. Preferred olefinic compounds employed in the practice of the invention are mono-olefins. Those mono-olefins having 4 up to about 30 carbon atoms with only one carbon-carbon double bond, and are capable of forming tertiary carbocations under the alkylation process conditions are especially preferred, because the possibility of multiple alkylation reactions with consequent formation of a mixture of products is minimized.

The especially preferred group of olefinic compounds useful in the practice of my invention can also be described by the formula

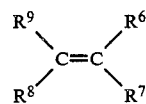

wherein each of $R^6$, $R^7$, $R^8$ and $R^9$ are independently selected from hydrogen and $C_1$ through $C_{10}$ alkyl or cycloalkyl radicals. In addition, $R^6$ and $R^7$ can be joined as part of a polymethylene radical or a halogen-, alkyl- or cycloalkyl-substituted polymethylene radical having about 2 to about 20 carbon atoms, i.e., a carbocyclic compound with an exocyclic double bond. Further, $R^6$ and $R^9$ can be similarly joined as part of a polymethylene radical or a halogen-, alkyl-, or cycloalkyl-substituted polymethylene radical having about 2 to about 20 carbon atoms, i.e., a carbocyclic compound with an endocyclic double bond.

Examples of olefinic compounds useful in the practice of the invention include isobutylene, 2-methyl-1-butene, 2-methyl-2-butene, 2,3-dimethyl-2-butene, neohexene (tertiary-butylethylene), diisobutylene (2,4,4-trimethyl-1-pentene), 2-butene, 2-pentene, 1-methylcyclohexene, 1-methylcyclopentene, 2-hexene, and the like.

The alkylated products of the invention find a wide range of uses, such as for example as reaction solvents, as chemical intermediates for the production of fragrance chemicals, as chemical intermediates for the production of herbicides and so on.

The catalyst employed in the process of the present invention consists essentially of aluminum halide and elemental iodine, although it should be recognized that additional catalyst components which do not detrimentally affect the performance of the alkylation catalyst can also be present. The aluminum halide component can be represented as $$AlX_3$$

wherein each X is independently selected from the halogens. Thus, suitable aluminum halide compounds include aluminum tribromide ($AlBr_3$), aluminum triiodide ($AlI_3$), aluminum chloride ($AlCl_3$) and the like and mixtures of any two or more thereof. Aluminum chloride is the presently preferred aluminum halide because it is readily available and provides a selective as well as a reactive catalyst.

The catalyst components, i.e. $AlX_3$ and $I_2$, can be combined in any suitable ratio as can be readily determined by one skilled in the art. For purposes of guidance, it is suggested that a weight ratio of $I_2:AlX_3$ of about 0.01:1 up to about 1:1 be employed. It is preferred, for most efficient use of reagents and for optimum catalyst performance, that a weight ratio of $I_2:AlX_3$ of about 0.1:1 to about 0.4:1 be employed.

The catalyst components can be combined in any suitable manner as readily determined by those skilled in the art. Thus, catalyst components can be dry mixed, slurried in a solvent which is not reactive under the reaction conditions employed, slurried in the reactant aromatic compound, slurried in an aliquot of the alkylated aromatic product or combined by other suitable techniques.

Although the catalyst can withstand the presence of small amounts of moisture, it is preferred that care be taken to exclude the presence of substantial amounts of moisture from the reaction medium. While optional, it is preferred that catalyst preparation as well as the alkylation reaction be carried out in an inert atmosphere, i.e., in the presence of a gas such as $N_2$, Ar and the like.

The molar ratio of olefinic compound to aromatic compound employed in the practice of the invention can vary broadly. In order to provide further guidance, it is suggested that a molar ratio of olefinic compound to aromatic compound of at least about 0.05:1 up to about 5:1 be employed. Ratios below the lower value provide low product yield based on the amount of starting material employed, while ratios above the upper value have a tendency to produce undesirable levels of by-products due to multiple alkylation reactions of the aromatic ring, olefin rearrangement and the like. Ratios of about 0.2:1 up to about 3:1 are preferred for efficient use of starting materials and minimum formation of by-products, which in turn simplifies the task of product recovery.

The alkylation reaction of the invention can be carried out in any suitable vessel which provides efficient contacting between the catalyst components and the reactants. For simplicity, a stirred batch reactor can be employed. The material of construction of the reaction vessel should be chosen so as to be resistant to the possibly corrosive nature of the catalyst. Thus, a glass-lined vessel, Hastelloy C or other resistant alloys as are known in the art are suitable. The major requirement which any reaction vessel must satisfy is the ability to provide rapid, efficient mixing since the alkylation reaction catalyzed by $AlX_3$—$I_2$ is frequently a very rapid reaction.

The molar ratio of $AlX_3$ to reactant aromatic compound can be readily determined by those skilled in the art. In order to provide guidance, it is suggested that a molar ratio of at least about 0.001 moles of $AlX_3$ per mole of reactant aromatic compound up to a molar ratio of about 1:1 be employed. Preferably, a molar ratio of about 0.01:1 to about 0.5:1 will be employed for most efficient utilization of reagents.

Because the alkylation reaction is generally quite rapid, temperature requirements for the alkylation reaction are quite modest. Broadly, a temperature range of about 0° up to about 130° C. is suitable. Where cyclialkylation is specifically desired, a temperature range of about 20° to about 80° C. is appropriate. The preferred temperature range for cyclialkylation is about 30° to about 65° C., while the preferred temperature range for simple aromatic ring alkylation is about 40° to about 100° C.

It is convenient as a means of temperature control to employ excess reactant aromatic compound or alkylated aromatic product or other diluents which are relatively inert to the reaction conditions employed. When the desired alkylation reaction is rapid and consequently required contact between catalyst and diluent is short, the stability of the diluent under the reaction conditions employed is not as critical as when longer reaction times are employed. In order to minimize by-product formation, however, it is preferred that diluents which do not undergo substantial isomerization, rearrangement, degradation or the like under the reaction conditions be employed. It is especially preferred to use alkylated aromatic product as the diluent for ease of product recovery.

The pressure at which reaction is carried out is not critical. If reaction is carried out in a sealed vessel, autogenous pressure is suitable, although higher or lower pressures can be employed. Reaction can also be carried out at atmospheric pressure in an open reaction vessel, in which case the vessel will preferably be equipped with a moisture trap to prevent significant exposure of catalyst to moisture.

Reaction time is generally quite short and is often dictated by the type of equipment employed. Sufficient time must be provided for thorough contacting of the aromatic compound, the olefinic compound and the catalyst. Although in theory there is no upper limit as to the reaction time which may be employed, reaction is generally quenched shortly after all reagents are contacted to prevent a significant degree of side reactions from occurring. Thus, depending on the type of reaction vessel employed and its stirring capabilities, etc., reaction time could be a matter of seconds to a matter of minutes. Reaction is then quenched and worked up as described in more detail below to prevent a significant degree of product isomerization or degradation from occurring in the continued presence of active catalyst.

Product mixture prepared in the above described manner is then contacted with at least one hydrocarbon soluble organometallic compound as described above and subjected to distillation in order to recover essentially colorless alkylated aromatic product.

In accordance with yet another embodiment of the present invention, novel compositions are provided consisting essentially of:

(a) at least one alkylaromatic hydrocarbon selected from the group consisting of:

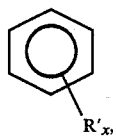

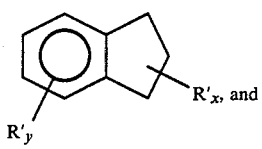

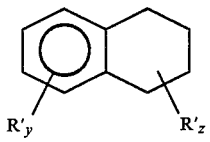

wherein each R' is independently a $C_1$-$C_{30}$ alkyl or cycloalkyl radical, x is an integer from at least 1 up to 6, y is an integer from 0 up to 4, and z is an integer from at least 1 up to 8;

(b) at least one iodine-containing compound selected from the group consisting of:
I$_2$, and
R—I wherein R is H or an organic radical having 1-20 carbon atoms, inclusive; and (c) 0.02-0.1 wt. % of a metal compound having the formula:

M—R'' wherein
M is Cu, Fe, Co, or Zn; and
R'' is an anionic organic radical having 2-30 carbon atoms such that M—R'' forms a salt which is at least sparingly soluble in said alkylaromatic hydrocarbon. Such compositions are useful means to store and/or ship alkylated aromatic compounds prior to purification by distillation and subsequent use as chemical intermediates, fragrance chemicals, and the like.

The invention is further illustrated by the following example.

EXAMPLE

Preparation and distillation of 1, 1, 3, 3, 5-Pentamethylindane (PMI)

To p-cymene (90 grams, 0.67 mole) was added 7.0 grams (0.05 mole) of anhydrous aluminum chloride and 2 grams (0.008 mole) of iodine under an atmosphere of nitrogen. The mixture was stirred rapidly and 48.5 grams (0.87 mole) of isobutylene was added over a period of 30 minutes while the temperature was maintained at 30°-35° C. with external cooling. Upon completion of the addition, the purple solution was quenched with water, then washed with aqueous sodium thiosulfate. An amber colored organic layer was separated from the aqueous wash. Additional washing with aqueous sodium hydroxide did not cause additional color changes.

Analysis by glc showed 52% conversion of the p-cymene and a 98.7% selectivity to PMI.

Samples of the PMI (generally 40 mL) were distilled through a 15 inch Vigreaux column at gradually reducing pressure, generally in the range of 125 down to 20 mm Hg. Results of treating a sample prior to distillation by additional washing or by the addition of small amounts (0.02-0.1 g) of a metal complex which was at least partially soluble in the PMI are noted in Table I.

TABLE I

| | | | Distillation of Pentamethylindane (PMI) | | | |
|---|---|---|---|---|---|---|
| | | | | Visual Appearance of Distillation Cuts** | | |
| Run | Second Wash Prior to Distillation | Added to Distillation Pot* | Forecut | First PMI Fraction | Second PMI Fraction | Heavies |
| 1 | aq. HCl | None | P | Bright P | P | Lt. O |
| 2 | aq. Na$_2$S$_2$O$_3$ | None | C | Lt. P | Lt. P | Lt. P |
| 3 | aq. NaOCl | None | P | P | P | P |
| 4 | None | NH$_4$Ce(SO$_4$)$_4$ | C | P | P | P |
| 5 | None | Cu(OAc)$_2$ | P | C | C | C |
| 6 | None | None | C | C | C | C (Note 1) |
| 7 | None | None | C | C | C | C (Note 1) |
| 8 | None | None | C | P | C | C (Note 2) |
| 9 | aq. Na$_2$S$_2$O$_3$ | None | C | P | P | P-O |
| 10 | None | None | P | P | P | P |
| 11 | None | CuAcac | C | C | C | |
| 12 | None | None | P | P | P | Ca. C |
| 13 | None | Cu$_2$O | Lt. P | Bright P | P-O | P |
| 14 | None | Co(III)Acac | P | Lt. P | L | L |
| 15 | None | Co(II)Acac | C | Lt. P | Lt. P | L |
| 16 | None | Fe(II)Acac | C | Y | Y | Y |
| 17 | None | Cu Acac | Lt. P | Lt. P | C | C |
| 18 | None | Cu Naphth. | C | Lt. P | | Y |
| 19 | aq. NaOH | Cu Naphth. | C | Lt. Y | | White Solid (Note 3) |
| 20 | None | Cu Acac | C | Lt. Y | — | |

TABLE I-continued

<table>
<tr><th colspan="6">Distillation of Pentamethylindane (PMI)</th></tr>
<tr><th></th><th></th><th></th><th colspan="3">Visual Appearance of Distillation Cuts**</th></tr>
<tr><th>Run</th><th>Second Wash Prior to Distillation</th><th>Added to Distillation Pot*</th><th>Forecut</th><th>First PMI Fraction</th><th>Second PMI Fraction</th><th>Heavies</th></tr>
<tr><td>21</td><td>None</td><td>Cu Naphth + CaO</td><td>C</td><td>Lt. Y</td><td></td><td>Lt. Y</td></tr>
<tr><td>22</td><td>None</td><td>Cu Naphth + CaO</td><td>C</td><td>C</td><td></td><td>Lt. Y</td></tr>
<tr><td>23</td><td>None</td><td>Fe(II)Acac</td><td>Lt. Y</td><td>Bright Y</td><td></td><td>Bright Y-O</td></tr>
<tr><td>24</td><td>None</td><td>Cu Naphth + Fe</td><td>C</td><td>ca. C</td><td></td><td>Lt. Y</td></tr>
<tr><td>25</td><td>None</td><td>Cu Naphth + CaO</td><td>C</td><td>ca. C</td><td></td><td>Lt. Y</td></tr>
<tr><td>26</td><td>None</td><td>Zn Acac</td><td>C</td><td>ca. C</td><td></td><td>Lt. Y</td></tr>
<tr><td>27</td><td>None</td><td>None</td><td>C</td><td>ca. C</td><td></td><td>Lt. Y (Note 4)</td></tr>
<tr><td colspan="7">Column washed with nitric acid, then water, and finally acetone</td></tr>
<tr><td>28</td><td>None</td><td>None</td><td>Dark</td><td>P-O</td><td></td><td>Y</td></tr>
<tr><td>29</td><td>None</td><td>Zn Acac</td><td>C</td><td>ca. C</td><td></td><td>Lt. Y</td></tr>
<tr><td>30</td><td>None</td><td>Cu Tallate</td><td>P</td><td>C</td><td>C</td><td>C</td></tr>
</table>

*OAc = Acetate; Acac = Acetylacetonate; Naphth = Naphthenate
**P = Pink; O = Orange; L = Lavender; Y = Yellow; C = Colorless; caC = nearly colorless
Notes:
(1) Trace of Cu(OAc)$_2$ in column
(2) Still small trace of Ca(OAc)$_2$ in column
(3) White solid is hydrindacene product
(4) Trace of Zn Acac in column The results presented in Table I demonstrate the effectiveness of such hydrocarbon soluble organometallic compounds as copper acetate, copper acetylacetonate, zinc acetate and the like for providing essentially colorless distilled product from a reaction mixture containing color-forming impurities.

The examples have been provided merely to illustrate the practice of my invention and should not be read so as to limit the scope of my invention or the appended claims in anyway. Reasonable variation and modification, not departing from the essence and spirit of my invention, are contemplated to be within the scope of patent protection desired and sought.

That which is claimed is:

1. A process for the preparation of alkylaromatic hydrocarbons which comprises:
   (1) contacting
   (a) at least one monocyclic, bicyclic or tricyclic aromatic compound having 6 up to 30 carbon atoms and
   (b) at least one olefinic compound having the formula

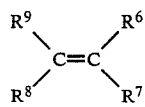

wherein each of $R^6$ through $R^9$ is independently selected from hydrogen and $C_1$ through $C_{10}$ alkyl or cycloalkyl radical; or $R^6$ and $R^7$ or $R^6$ and $R^9$ can be joined as part of a polymethylene or alkyl- or cycloalkyl-substituted polymethylene radical having two to about 20 carbon atoms, wherein said olefinic compound has 4 up to 30 carbon atoms, and wherein said olefinic compound is capable of forming a teritary carbocation under the process conditions in the presence of a catalyst consisting essentially of
   (i) $AlX_3$ and
   (ii) $I_2$;
where each X is individually selected from the halogens;
   (2) washing the reaction mixture produced in step (1) with caustic and separating a washed organic layer therefrom;
   (3) adding 0.02 to 0.10 wt % of a metal compound to the washed organic layer obtained from step (2); and thereafter
   (4) subjecting the mixture produced in step (3) to distillation, wherein the complex $MI_n$ formed upon distillation is non-volatile and essentially non-decomposable under distillation conditions.

2. A process in accordance with claim 1 wherein metal compound is provided as a compound having the formula:

$$M-R''$$

wherein
M is selected from the group consisting of Cu, Fe, Co, and Zn; and
R'' is an anionic organic radical having 2-30 carbon atoms such that R''—M forms a salt which is at least sparingly soluble in the alkylaromatic hydrocarbon product produced in step (1).

3. A process in accordance with claim 1 wherein said (a) aromatic compound has the formula

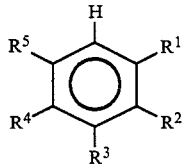

wherein each $R^1$, $R^2$, $R^3$, $R^4$, and $R^5$ is independently selected from hydrogen, and $C_1$ through $C_{10}$ alkyl or cycloalkyl radicals.

4. A process in accordance with claim 1 wherein the weight ratio of (ii):(i) is about 0.01–1:1 and the molar ratio of (i):(a) is about 0.01–0.5:1.

5. A process in accordance with claim 2 wherein M is Zn.

6. A process in accordance with claim 2 wherein R'' is selected from the group consisting of:
acetylacetonate,
naphthenate,
tallate,
sulfonate, and
$ACO_2$—;
wherein A is a $C_1$-$C_{10}$ carbon radical.

* * * * *